United States Patent [19]
Buck et al.

[11] 4,456,014
[45] Jun. 26, 1984

[54] FLOW RESTRICTOR

[75] Inventors: Keith E. Buck, Alamo; Irving C. Chase, El Sobrante; Marius J. Morin, Westlake Village, all of Calif.

[73] Assignee: Thoratec Laboratories Corporation, Berkeley, Calif.

[21] Appl. No.: 449,540

[22] Filed: Jan. 3, 1983

[51] Int. Cl.³ .............................................. A61B 5/08
[52] U.S. Cl. .................................... 128/719; 128/718; 73/863.86; 73/863.23
[58] Field of Search ............... 128/716, 717, 718, 719, 128/730, 765, 204.22, 205.23; 604/246; 73/863.23, 863.86

[56] References Cited

U.S. PATENT DOCUMENTS

| | | | |
|---|---|---|---|
| 2,515,470 | 7/1950 | Prytz | 604/246 |
| 3,530,850 | 9/1970 | Edwards, Jr. | 128/716 |
| 3,683,700 | 8/1972 | Wilfong | 73/863.86 |
| 3,858,449 | 1/1975 | Singer | 73/863.86 |
| 3,858,573 | 1/1975 | Ryan et al. | 128/730 |
| 4,014,216 | 3/1977 | Thornton et al. | 73/863.23 |
| 4,046,593 | 9/1977 | Au et al. | 73/863.23 |
| 4,221,130 | 9/1980 | Burrows | 128/719 |

FOREIGN PATENT DOCUMENTS 1032177 6/1966 United Kingdom ................ 128/719

*Primary Examiner*—Henry J. Recla
*Attorney, Agent, or Firm*—Lothrop & West

[57] ABSTRACT

For restricting the flow of breathing gas between a patient's breathing tube and a breathing gas analyzer, there is provided a fitting extending into the breathing tube. The fitting preferably has a restricted inlet volume opening through a filter and through a capillary tube into an outlet connectable to the gas analyzer.

6 Claims, 1 Drawing Figure

U.S. Patent
Jun. 26, 1984
4,456,014
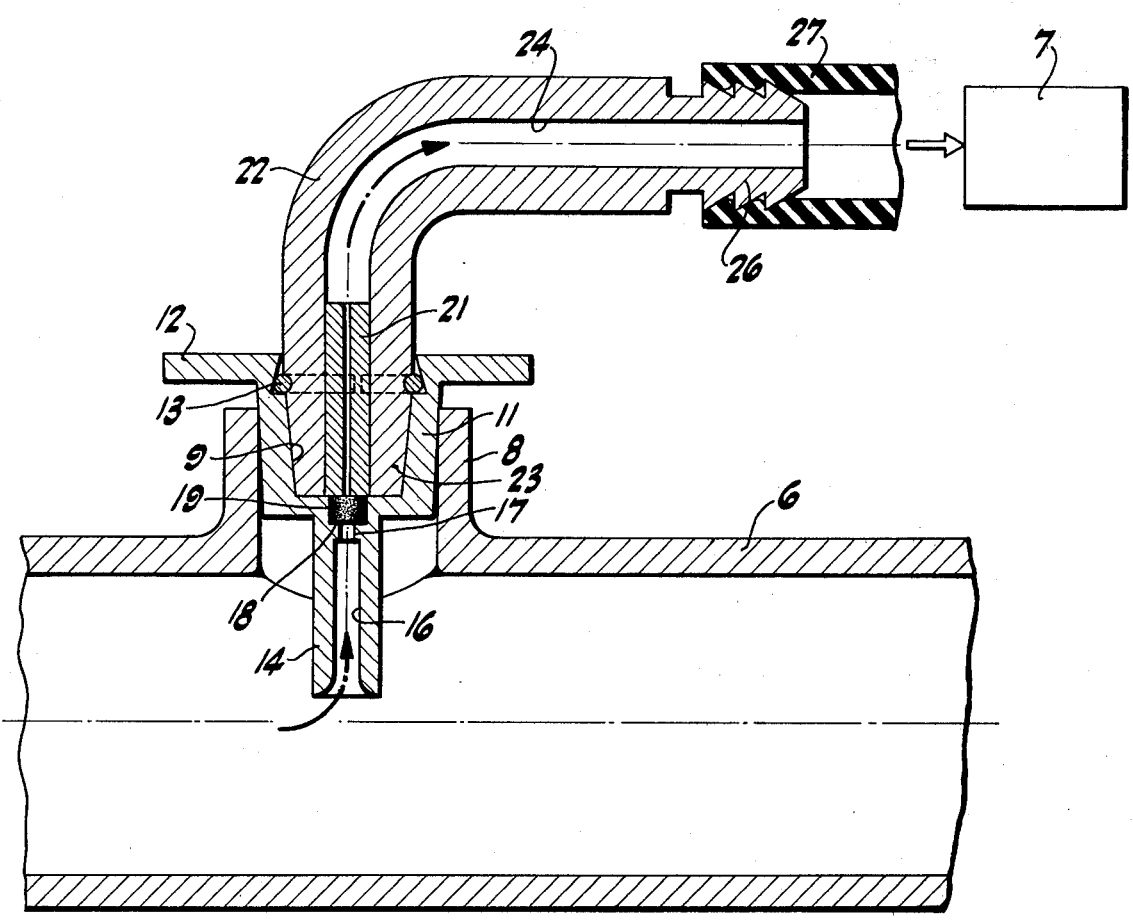

FLOW RESTRICTOR

BRIEF SUMMARY OF THE INVENTION

A flow restrictor especially for use in breathing gas analysis includes a (preferably glass) capillary tube as a flow restricting device and also includes a filter on the upstream side of the capillary tube with the filter and tube being removably interposed between an inlet from a patient's breathing tube and the gas analyzer itself.

PRIOR ART

No prior art is presently known to the applicants.

BRIEF DESCRIPTION OF THE DRAWING

The drawing is a diagrammatic view largely in cross-section showing the flow restrictor in a customary environment between a breathing tube and a tube extending to a gas analyzer, certain portions being broken away to reduce the size of the FIGURE.

DETAILED DESCRIPTION

In many instances, particularly with hospitalized patients, there is provided a breathing apparatus so that the patient may be supplied with air enriched with oxygen and may exhale under some monitoring. It is of interest in many cases to analyze the exhaled breath. This is accomplished by means of a gas analyzer. For this purpose only a small fraction of the total volume exhaled need be considered, but the examination or monitoring may extend almost continuously over a protracted breathing time, sometimes a matter of days.

In a representative installation, there is provided a breathing line 6 in the nature, usually, of a flexible tube. For example, at its left end this is connected to a mask or breathing device utilized by the patient and at its right end is connected for general atmospheric discharge. The patient may be given oxygen in various ways, often by utilization of the breathing line 6.

There is likewise provided a gas analyzer 7 represented diagrammatically. This is standard equipment effective upon a sample of gas (breath) to afford a read-out of the content thereof; for example, the percentage of $CO_2$ at any one time or continuously.

The tube 6 is afforded a lateral boss 8 conveniently formed integrally therewith and having a conical bore 9 communicating with the interior of the tube 6. Adapted readily to fit into the conical bore is a bushing 11 having a finger-engaging portion 12 and a snap ring 13 arranged so that the bushing can be easily introduced into and removed from the boss 8 with no leakage therebetween.

The bushing is particularly extended well into the interior of the sampling line 6 by means of an inlet tube 14 of generally circular, cylindrical form and long enough to extend approximately to the center of the tube 6. The inlet tube 14 has an interior bore 16 of relatively small diameter so that the total volume of the space within the extension tube 14 is small. There is little or no room for gas mixing therein when the contents of the tube 6 change markedly from one gas to another, such as from oxygen on the inhalation cycle to carbon dioxide on the exhalation cycle.

The tube 14 is provided with a rather large cavity 17 leaving a ledge 18 to support a filter 19 in position between the ledge and a capillary tube 21. Conveniently, the capillary tube is formed of glass and is held in place by an outlet tube 22 having a tapered end 23 adapted to fit into a corresponding taper in the bushing 11. The outlet tube 22 has a through bore 24 leading to a fitting 26 receptive of a flexible conduit 27 leading to the analyzer 7.

With this arrangement there is provided at the analyzer 7 a somewhat below atmospheric pressure so that there is a tendency for gas to travel from the line 6 and through the inlet tube 14 and the filter 19. Such flow then continues through the capillary tube 21, but is restricted in amount by the capillary tube. The restriction is due not only to the relatively small diameter of the capillary tube 21 but also to its length. After this flow restriction, gas arriving within the passage 24 is able to flow at a reasonable rate through the connector 27 to the gas analyzer 7.

Particularly the exhalation in the tube 6 carries with it some moisture, but it has been found by experience that the filter 19 serves as a moisture-gas separator and acts as a barrier to further flow of moisture toward the gas analyzer. This may occur during use or over a period of days. Thus, the interior of the capillary tube 21 remains dry and serves consistently as an appropriate restriction. Because it is of glass, the capillary is readily constructed to the desired interior diameter and is quite inexpensive. It is readily replaced when necessary with a comparable unit so that the restriction of flow is always about the same.

After extended use, there is no difficulty in withdrawing the bushing 11 along with the tube 14, the filter 19, and the capillary tube 21 and disconnecting the tube 22 and the tube 27. The tube 24 with the old capillary and filter portions can be easily discarded. That bushing can then be replaced by a complete and new unit. There is no necessity for any calibration of the new setup since the capillary tube 21 effects substantially the same amount of restriction. There is in this fashion afforded a way of sampling breathing gases from the customary breathing tube and furnishing an appropriate sample to a gas analyzer, but without carrying over undue moisture and without varying the quantity of flow, even though the connecting unit is replaced from time to time.

We claim:

1. A flow restrictor for use with a gas analyzer comprising a conduit adapted to conduct respiration gases; an inlet tube extending within said conduit and defining an inlet volume; an outlet tube forming a junction with said inlet tube; and a capillary tube within said outlet tube, extending substantially to said junction and open at one end to said inlet tube and at the other end to said outlet tube.

2. A flow restrictor as in claim 1 including a filter in said inlet tube substantially at said junction.

3. A flow restrictor as in claim 2 including means in said inlet tube for holding said filter against the adjacent end of said capillary tube.

4. A flow restrictor as in claim 1 in which said capillary tube is glass.

5. A flow restrictor especially for use with a gas analyzer comprising a conduit having an annular boss in one wall thereof, a bushing fitted into said annular boss, an inlet tube on said bushing extending into said conduit, an inlet passageway extending through said inlet tube and bushing, an outlet tube having one end extending into said bushing in substantial alignment with said inlet passageway and an opposite end adapted to be connected to a gas analyzer, and a capillary tube mounted in said outlet tube adjacent said one end and having a first end in substantial abutment with said bushing and an opposite end in communication with said outlet tube.

6. A flow restrictor as in claim 5 in which said inlet tube has a relatively small volume relative to the volume of said inlet tube.

* * * * *